United States Patent [19]

Woods, Jr.

[11] 4,358,961

[45] Nov. 16, 1982

[54] METHODS AND APPARATUS FOR TESTING RUPTURE STRENGTH OF TUBULAR PARTS

[75] Inventor: William L. Woods, Jr., Keithville, La.

[73] Assignee: Western Electric Company, Inc., New York, N.Y.

[21] Appl. No.: 222,428

[22] Filed: Jan. 5, 1981

[51] Int. Cl.³ .............................................. G01N 3/08
[52] U.S. Cl. ........................................ 73/827; 73/818
[58] Field of Search ............. 73/818, 825, 827, 150 A, 73/788, 826, 837, 821

[56] References Cited

U.S. PATENT DOCUMENTS

| | | | |
|---|---|---|---|
| 3,690,141 | 9/1972 | Brownbill | 72/370 |
| 3,992,928 | 11/1976 | Thoms | 73/821 |
| 4,047,425 | 9/1977 | Handy et al. | |
| 4,122,704 | 10/1978 | Lutenegger et al. | 73/822 |
| 4,300,397 | 11/1981 | Kempen | 73/818 |

Primary Examiner—Jerry W. Myracle
Attorney, Agent, or Firm—R. F. Kip, Jr.; J. L. Landis

[57] ABSTRACT

A tubular piece part (10) is tested to determine the rupture strength of the part when subject to lateral expansion (F) with respect to a bore (11) of the part. In one example, a tubular segmented collet (21) is placed in the bore of the part, and a tapered pin (23) is forced a predetermined distance into the collet (X) so as to expand the collet and part radially outward by a predetermined amount. The peak force required to so expand the collet is measured (57) so as to provide an indication of the rupture strength of the part, and particularly of the weld strength of a molded plastic tube having a radial weld line (W). In particular, this method provides an indication of the likelihood that the part will fail prematurely in the field, after subsequent assembly of the part with an insert member (17) that is force fit into the bore.

11 Claims, 5 Drawing Figures

METHODS AND APPARATUS FOR TESTING RUPTURE STRENGTH OF TUBULAR PARTS

TECHNICAL FIELD

This application relates generally to techniques and equipment for testing the rupture strength of a tubular part that is subject to radial expansion with respect to a longitudinal bore of the part, and more particularly for testing the weld strength of a molded plastic tube or sleeve having a radial weld line and a bore into which an insert member is force fit so as to tend to rupture the part along the weld line.

BACKGROUND OF THE INVENTION

In the manufacture of general purpose telephone sets, a molded plastic housing of the set is assembled with a base member of the set by threaded fasteners, such as machine screws. For this purpose, the housing is formed with a series of upstanding tubular plastic sleeves or bosses, each having an axial bore into which an insert member, such as an internally threaded tubular receptacle for receiving the machine screw, is to be force fit during manufacture of the housing. In the plastics molding operation, the boss is formed with a weld line extending radially across an annular wall of the boss at one point along the circumference and extending the length of the boss. When the receptacle is subsequently force fit into the bore of the boss, radially expansive forces are exerted on the walls of the boss tending to rupture the boss at the weld line. Where the part does not rupture during manufacture, strain is set up in the expanded plastic material that tends to rupture the part at a later time. When the material is unduly weak, the bosses have a tendency to crack prematurely in the field, after the telephone set has been installed on a customer's premise.

SUMMARY OF THE INVENTION

A specific object of the invention is to provide methods and equipment for testing the weld strength of such molded plastic tubular parts, so as to provide an indication of weak parts that will fail during subsequent assembly or that will be so weakened during assembly that the parts are likely to rupture prematurely in the field.

More general objects are to provide techniques for testing the rupture strength of a tubular part that is subject to radial expansion with respect to a longitudinal bore of the part.

With the foregoing and other objects in view, methods and apparatus in accordance with certain features of the invention are designed for testing the rupture strength of a tubular part that is subject to radial expansion with respect to a longitudinal bore of the part. In accordance with the improved construction and method, an expansible tubular collet is placed in the bore of the part to be tested, and an expanding member is then forced a predetermined distance into the collet so as to expand the collet and thus the walls of the part radially outward by a predetermined amount. The peak force required to so expand the collet is measured to provide an indication of the rupture strength of the part when subjected to radial expansion.

In one example, the part comprises a molded plastic cylindrical tube having a radial weld line extending across the wall of the tube, wherein the tube tends to rupture along the weld line when the tube is subsequently assembled with an insert member that is force fit into the bore of the tube. In this example, the peak force reading provides an indication of the weld strength of the tube and, where the weld does not rupture during the test, an indication of the likelihood that the part will fail prematurely in the field. In particular, it has been determined that the parts most likely to crack early in the field require less force to expand the part during the test.

Preferably, the collet is a segmented cylindrical collet having an outer periphery shaped to fit coaxially into the bore of the part and a conically tapered axial bore. In this example, the expanding member comprises a conically tapered pin that is driven by an air cylinder assembly a fixed distance into the collet to provide the predetermined expansion of the collet and part. In this case, the peak pressure required to drive the pin the fixed distance into the collet is recorded, to provide an indication of the weld strength and stress-to-rupture characteristics of the part.

Other objects, advantages and features of the invention will be apparent from the following detailed description of a specific example and embodiment thereof, where read in conjunction with the accompanying drawings.

DETAILED DESCRIPTION

Figure 1:
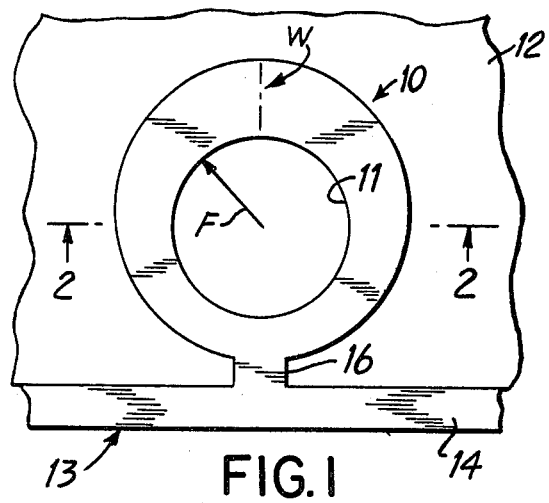
FIG. 1 is a plan view of a portion of a telephone set housing, including a tubular plastic boss to be tested in accordance with the invention.
Figure 2:
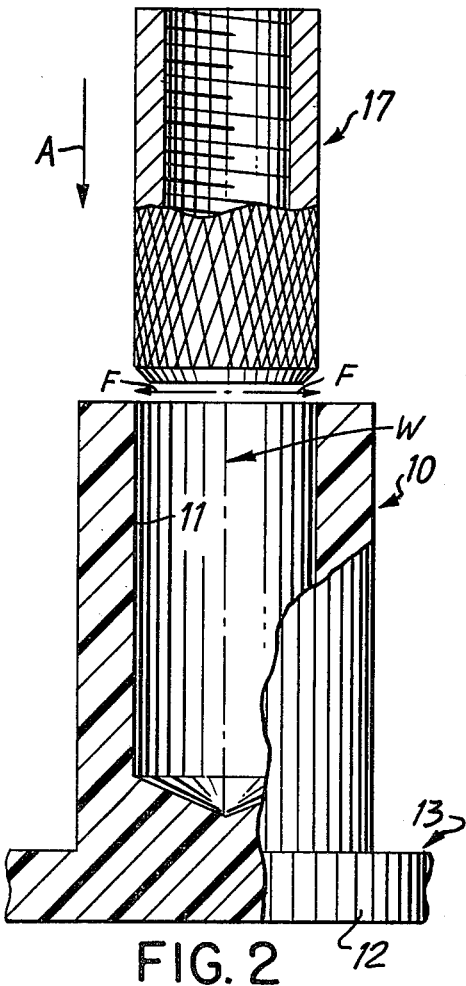
FIG. 2 is a vertical section along line 2—2 of FIG. 1, also illustrating a fastener member that is to be assembled with the boss.

Referring now in detail to the drawings, and particularly to FIGS. 1-2, methods and apparatus in accordance with one specific embodiment of the invention are designed for testing the rupture strength of a tubular part, such as a molded plastic tube or boss 10 having a longitudinal bore 11, wherein the part is subject to radial expansion with respect to the bore (arrows F—F). In this context, the phrase "radial expansion" is intended generally to signify expansion laterally outward in all directions from a central axis of the part, such as the axis of the bore 11 in the example illustrated in FIGS. 1-2. In this example, a plurality of the bosses 10 are formed at intervals along the bottom wall 12 of a molded plastic housing 13 for a general purpose telephone set, so that each boss 10 extends vertically upward from the bottom wall 12 as illustrated in FIG. 2. Each boss is joined to a side wall 14 of the housing, by a connecting web 16 as illustrated in FIG. 1. The housing, including the bosses 10, is molded from a suitable plastic material such as an ABS molding compound (acrylonitrile-butadiene-styrene).

In use, an insert member, such as a metal fastener 17, is subsequently assembled with each boss 10; for example, to provide for subsequent mechanical connection of other elements to the housing 13. In this example, the fastener 17 is an internally threaded tubular metal receptacle that is force fit into the bore 11 (arrow A), to provide a receptacle for machine screws that will later fasten the housing 13 to the base (not shown) of the telephone set. In this example, both the fastener 17 and bore 11 are cylindrical, with the outer diameter of the fastener being slightly oversize with respect to the inner diameter of bore and with the exterior surface of the fastener being knurled so as to provide a preset interference fit between the fastener and the boss.

The boss is formed by standard injection molding techniques, and includes an invisible weld line designated "W" formed during the molding process and extending radially across the wall of the boss at one point along the circumference thereof, as indicated in FIG. 1, and also running the length of the boss as indicated by the phantom line W in FIG. 2. In this example, the boss 10 has a tendency to rupture along the weld line when radial expansive forces F subsequently are applied to the inner walls of the boss, such as when the fastener 17 is force fit into the bore 11. Where as in most cases the boss does not so fail during manufacture of the telephone set, the joint W may still be so weakened by the assembly step that it will crack prematurely in the field, after the set has been shipped to a customer and placed in service. In particular, the radially expansive forces F applied to the walls of the boss by the insertion of the fastener set up strain in the material of the plastic, tending to rupture the part along the weld line W. Depending on the manufacturing and material parameters, different parts will have different "stress-to-rupture" characteristics, this being the time of ultimate rupture if a given force is maintained on the part.

One technique that has helped to some extent in providing stronger joints is to form the boss 10 slightly eccentric, with the center of the bore 11 being slightly offset from the center of the outer cylinder, as depicted in somewhat exaggerated fashion in FIG. 1, so as to provide a slightly greater wall thickness in the area of the weld line W than at the position 180° away from the weld.

In any case, it is highly desirable to be able to detect weak parts that will tend to have a short field life, and a principal object of this invention is to provide methods and apparatus for testing the rupture strength of such parts and, in the particular example illustrated, for testing the weld strength of molded plastic bosses 10 such as described above, and for providing an indication of the likelihood that the part will fail (crack) prematurely in the field, after subsequent assembly of the part 10 with the insert member 17.

Figure 3:
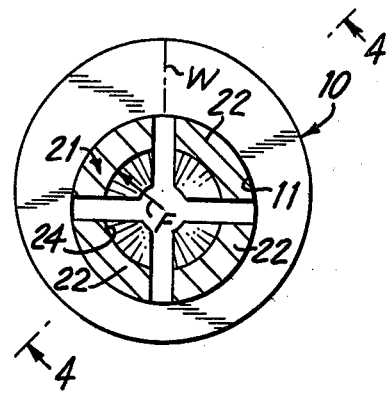
FIG. 3 is a top view of the boss as in FIG. 1, illustrating also portions of an expansible collet that is inserted into the boss during the testing operation, taken generally along the line 3—3 of FIG. 4.
Figure 4:
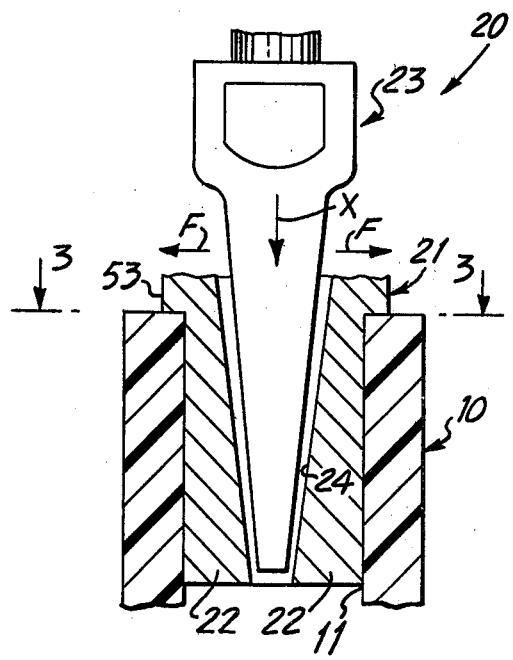
FIG. 4 is a vertical section along line 4—4 of FIG. 3, illustrating also a tapered pin that is inserted into the collet during the testing operation.

Referring now to FIGS. 3-4, testing apparatus 20 in accordance with certain features of the invention includes an expansible tubular collet 21 having an outer periphery shaped to permit placing of the collet into the bore 11 as illustrated in FIGS. 3-4. In this example, the collet 21 is a segmented tubular collet composed of four arcuate segments 22—22 defining a cylindrical outer periphery congruent with respect to the bore 11. An expanding member is provided, such as a conically tapered pin 23, that is forced a predetermined distance into the collet 21 (arrow X) so that the collet segments expand radially outward (arrows F) against the walls of the bore 11 so as to expand the walls of the boss radially outward by a predetermined amount, thus tending to rupture the boss along the weld line W and simulating the hoop stress that occurs in the boss during a fastener assembly operation as described above.

In the example illustrated, the collet is formed with a mating conically tapered axial bore 24, so that insertion of the conically tapered pin 23 into the bore 24 of the collet 21 exerts a gradually increasing force on the collet 21, due to the resistance of the boss, to expand the boss 10 correspondingly outward. In accordance with the principles of this invention, it has been determined, that by measuring the peak force required to drive the pin 23 a predetermined distance into the collet, thus expanding the walls of the boss by a fixed amount, an indication is provided of the rupture strength of the part, and of weld-life efficiency of parts that do not fail during the test, as discussed in further detail hereafter.

Figure 5:
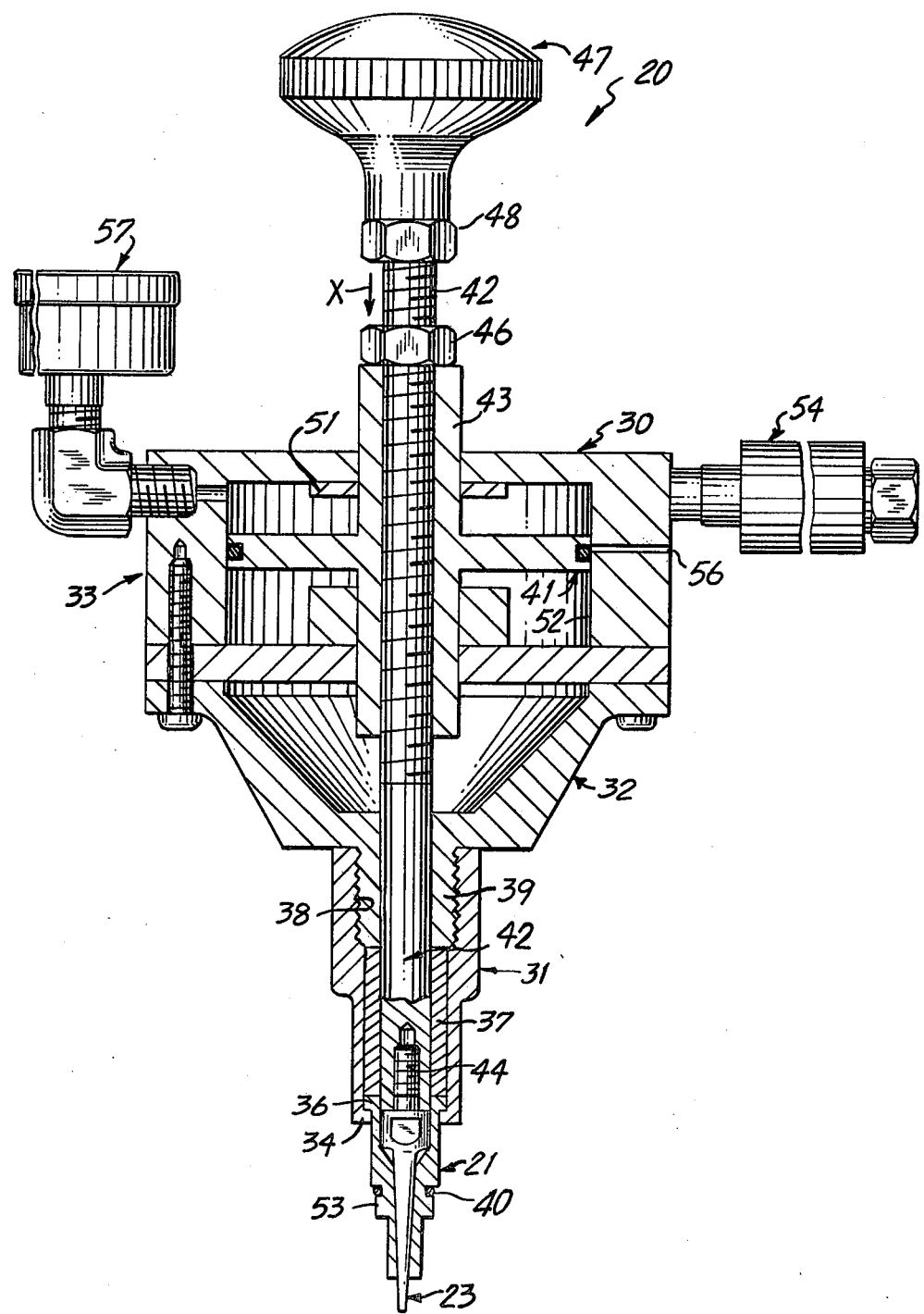
FIG. 5 is a vertical section of an air-cylinder operated testing apparatus in accordance with one specific embodiment of the invention.

Referring now to FIG. 5, a complete testing apparatus 20 in accordance with one specific embodiment of the invention includes a generally conventional air cylinder mechanism 30 for mounting the collet 21 and pin 23 in the required coaxial relationship, and for advancing the pin with respect to the collet during the testing operation as described above. In this example, the collet 21 is detachably fastened at the lower end of the mechanism 30, as illustrated in FIG. 5, by a threaded locking sleeve 31, which is fastened to a mounting flange assembly 32 bolted to the lower surface of the cylinder housing 33. For this purpose, the locking sleeve 31 includes an inwardly turned annular flange 34 at the lower end thereof, which supports an outwardly oriented annular flange 36 at the upper end of the collet 21; and a spacer sleeve 37 is positioned within the locking sleeve 31 on top of the collet flange 36 as shown. This mounting allows for float of the collet 21, to prevent binding and to provide for extraction of pin 23. The locking sleeve 31 is formed with a threaded bore 38 at the upper end thereof, which is screwed onto an externally threaded annular extension 39 of the mounting flange 32 so as to securely fasten the collet assembly coaxially to the cylinder housing 33 as illustrated. A resilient O-ring 40 is positioned in a circumferential groove formed in the collet segments 22 approximately midway along the length thereof, so as to normally bias the segments together to a closed position, when the segments are not being expanded by the pin.

The tapered pin 23 is connected to the piston (41) of the cylinder assembly 30 and is coaxially mounted within the collet 21 and locking sleeve 31 for reciprocating movement of the pin 23 with respect to the collet 21 as previously described. This connection includes an elongated cylindrical connecting rod 42 that is fastened near its upper end within an elongated sleeve portion 43 of the piston 41, and having a cylindrical bore at its lower end into which a threaded extension 44 at the upper end of the pin 23 is fastened as illustrated in FIG. 5. The connecting rod 42 is slideably mounted coaxially within the mounting flange 32 and spacer sleeve 37 to permit reciprocation of the rod 42 and pin 23 with respect to the fixed portions of the cylinder assembly 30.

The upper end of the connecting rod 42 is threaded, and the rod is connected in a desired position to the upper end of the piston sleeve 43 by a jam nut 46, which allows the vertical position of the rod 42 and pin 23 with respect to piston 41 to be adjusted so as to preset a desired zero position of the pin 23 with respect to the collet. A knurled plastic knob 47 is fastened to the upper end of the rod 42 by a second jam nut 48, which allows return and movement of the piston 41 and pin 23 with respect to the cylinder assembly 30.

In the pre-test position of the device, the piston 41 is initially positioned in a fully up, retracted position with the piston engaging a stop ring 51 at the upper end of the cylinder bore (52). To operate the device, the testing apparatus is assembled with a boss 10 to be tested, as illustrated in FIG. 4, with a flange portion 53 of the collet positioned against the upper surface of the walls of the boss 10. To operate the device 20, an air pressure source (not shown) is connected by a three-way sleeve valve 54 to apply compressed air through inlet ports at the upper end of the cylinder bore 52, so as to drive the piston 41 downward in the cylinder 30, thus forcing the pin 23 downward into the collet 21 as previously described. After the piston 41 has been driven a preset distance such as 0.40 inches (approximately 1.0 cm) in a typical example, the piston passes a series of circumferential vent holes 56 formed in the cylinder wall so as to release the pressure in the cylinder, thus halting further advancement of the piston and terminating the test operation at that point. The pin 23 and piston 41 assembly may be retracted to the initial, up position after the test, either manually by pulling up on the knob 47, or automtically by applying air pressure to the lower end of the cylinder bore 52.

A peak-pressure indicating gage 57 is connected to the cylinder bore 52 along the upper end thereof, so as to indicate the maximum pressure applied to the piston 41 during the test operation, thus providing an indication of the applied force F that was necessary to expand each particular boss 10 by the preset amount as described above, or to rupture the boss in those cases where the boss cracks during the test. With this process, stress/strain characteristics can be developed empirically for good, marginal, and bad parts of any given type to be tested. For example, in a typical embodiment in which a 0.280 inch diameter pin 23 (approximately 7.1 mm) is forced into a 0.250 inch diameter collet bore 24 (approximately 6.4 mm), a defective boss may rupture at 25 psig applied pressure (approximately 35 grams/square meter) prior to full insertion of the pin 23 into the collet 21. A good part will expand fully at an applied pressure of 50 psig and upwards (70 grams/square meter). If the part does not crack during the test, but expands too easily to the 0.280 dimension, for example, between 35-45 psig applied pressure (50-65 grams/square meter), this indicates that the part is marginal and is likely to fail prematurely in the field, particularly to pull out of the insert 17 in FIG. 1.

In view of the foregoing description, it should be apparent that there has been provided a low cost, simple and effective method and apparatus for testing the rupture strength of tubular parts, and particularly for testing the weld strength of molded plastic tubes or sleeves of the type described. In the development of the process, such tests can be run routinely on every lot of parts as a process check, or they can be run on a spot basis as desirable. Also, trends in the pressure-expansion characteristics of the parts can be fed back to the manufacturing process line to permit variation of the molding process or checking of the quality of molding compound, so as to improve the strength characteristics of the parts being molded.

While one specific embodiment of the invention has been described in detail above, it should be apparent that various modifications can be made from the specific details described, without departing from the spirit and scope of the invention.

What is claimed is:

1. A method of testing the rupture strength of a tubular part comprising a molded plastic cylindrical tube having a weld line extending radially across the wall of the tube at one point along the circumference thereof and extending the length of the tube, the tube being subject to radial expansion with respect to the longitudinal bore of the tube and having a tendency to rupture along the weld line when the tube is subsequently assembled with an insert member that is force fit into the bore of the tube, which method comprises:
   (a) placing an expansible tubular collet in the bore;
   (b) forcing an expanding member a predetermined distance into the collet so that the member expands the collet and the collet expands the walls of the part radially outward by a predetermined amount; and
   (c) measuring the peak force required to so expand the collet to provide an indication of the rupture strength of the tube, the peak force reading providing an indication of the weld strength of the tube and, where the weld does not rupture during the forcing step, an indication of the liklihood that the tube will fail prematurely in the field after subsequent assembly of the tube with the insert member.

2. A method as recited in claim 1, wherein the forcing step includes inserting a conically tapered pin the predetermined distance into a conically tapered axial bore of a segmented tubular collet having an outer peripheral surface adapted to fit coaxially into the bore of the tube.

3. A method as recited in claim 2, wherein the forcing step further includes applying air pressure to an air cylinder having a reciprocable piston coupled to one end of the pin, the peak force reading being the peak air pressure required to drive the pin through the predetermined distance.

4. A method as recited in claim 1, wherein the tube is molded so that the bore of the tube is eccentric with respect to the outer periphery of the tube and so that the weld line is located adjacent to the area of maximum wall thickness.

5. Apparatus for testing the rupture strength of a tubular part subject to radial expansion with respect to a longitudinal bore of the part, which comprises:
   an expansible tubular collet adapted to be placed in the bore of the part;
   an expanding member adapted to be forced into the collet so that the member expands the collet and the collet expands the walls of the part radially outward when the member is forced into the collet;
   means for forcing the expanding member a predetermined distance into the collet so that the collet and part are thereby expanded radially outward by a predetermined amount; and
   means for indicating the peak force required to so expand the collet to provide an indication of the rupture strength of the part.

6. Apparatus as recited in claim 5, wherein:
   the part comprises a molded plastic cylindrical tube having a weld line extending radially across the wall of the tube at one point along the circumference thereof and extending the length of the tube, the tube having a tendency to rupture along the weld line when the tube is subsequently assembled with an insert member that is force fit into the bore of the tube; and the peak force reading provides an indication of the weld strength of the tube and, where the weld does not rupture during the forcing operation, an indication of the likelihood that the tube will fail prematurely in the field after subsequent assembly of the tube with the insert member.

7. Apparatus as recited in claim 5 or claim 6, wherein:

the collet comprises a segmented tubular collet having an outer peripheral surface adapted to fit coaxially into the bore of the tube and having a conically tapered axial bore; and the expanding member comprises a conically tapered pin having a mating taper and adapted to be inserted axially into the collet so as to expand the collet by the predetermined amount.

8. Apparatus as recited in claim 7, wherein the means for forcing the pin into the collet comprises:

an air cylinder having a reciprocable piston;

means for coupling an outer end of the pin to the piston for movement therewith;

means for applying air pressure to the cylinder to drive the pin into the collet;

means for venting the cylinder after the pin has been driven the predetermined distance into the collet; and a gage connected to the cylinder for providing a peak pressure reading during the stroke of the piston, this being an indication of the peak force required to expand the collet.

9. Apparatus as recited in claim 8, further comprising means for fastening the collet to one end of the cylinder housing coaxially about the pin-coupling means.

10. Apparatus as recited in claim 9, further comprising means for adjustably mounting the pin to the piston so that the initial position of the pin with respect to the collet can be preset at a desired position in order to provide adjustment of the force exerted by the pin for a given stroke of the piston.

11. Apparatus as recited in claim 6, wherein the bore of the tube is eccentric with respect to the outer periphery of the tube, with the weld line located adjacent to the area of maximum wall thickness.

* * * * *